United States Patent
Yoshioka et al.

(10) Patent No.: US 9,075,023 B2
(45) Date of Patent: Jul. 7, 2015

(54) WIRE ROPE FLAW DETECTOR

(75) Inventors: Takashi Yoshioka, Chiyoda-ku (JP);
Yoshinori Miyamoto, Chiyoda-ku (JP);
Atsushi Mitsui, Chiyoda-ku (JP);
Masahiko Hida, Chiyoda-ku (JP);
Toyohiro Noguchi, Chiyoda-ku (JP)

(73) Assignee: MITSUBISHI ELECTRIC CORPORATION, Chiyoda-Ku, Tokyo (JP)

(*) Notice: Subject to any disclaimer, the term of this patent is extended or adjusted under 35 U.S.C. 154(b) by 75 days.

(21) Appl. No.: 14/112,377

(22) PCT Filed: Jun. 7, 2011

(86) PCT No.: PCT/JP2011/063028
§ 371 (c)(1),
(2), (4) Date: Oct. 17, 2013

(87) PCT Pub. No.: WO2012/169008
PCT Pub. Date: Dec. 13, 2012

(65) Prior Publication Data
US 2014/0035569 A1 Feb. 6, 2014

(51) Int. Cl.
*G01N 27/90* (2006.01)
*G01N 27/83* (2006.01)
*G01N 27/82* (2006.01)

(52) U.S. Cl.
CPC ............... *G01N 27/83* (2013.01); *G01N 27/82* (2013.01)

(58) Field of Classification Search
CPC ...................................................... G01N 27/90
USPC .................................................... 324/242
See application file for complete search history.

(56) References Cited

U.S. PATENT DOCUMENTS

| 5,550,468 | A | 8/1996 | Haberlein et al. | |
| 7,982,458 | B2 * | 7/2011 | Yoshioka et al. | 324/240 |
| 8,164,329 | B2 * | 4/2012 | Yoshioka et al. | 324/240 |
| 2007/0222438 | A1 * | 9/2007 | Reeves | 324/240 |

FOREIGN PATENT DOCUMENTS

| JP | 6-324020 A | 11/1994 |
| JP | 9-210968 A | 8/1997 |
| JP | 3143572 U | 7/2008 |
| JP | 2010-236928 A | 10/2010 |

OTHER PUBLICATIONS

International Search Report (PCT/ISA/210) mailed on Sep. 13, 2011, by the Japanese Patent Office as the International Searching Authority for International Application No. PCT/JP2011/063028.

* cited by examiner

*Primary Examiner* — Bot Ledynh
(74) *Attorney, Agent, or Firm* — Buchanan Ingersoll & Rooney PC (57) ABSTRACT

A wire rope flaw detector that is capable of accommodating a plurality of wire rope diameters and is inexpensive includes at least two magnetic sensor units that are integrated with a magnetizer and include planer coils placed opposite to each other with a magnetic circuit generated by the magnetizer in between, in the direction almost parallel to the magnetic circuit in a predetermined section of a wire rope. The detector further includes an adjuster capable of changing the distance between the at least two magnetic sensor units depending on the diameter of the wire rope.

9 Claims, 13 Drawing Sheets

C-C CROSS SECTION

FIG.4

D-D CROSS SECTION

FIG.13

WIRE ROPE FLAW DETECTOR

TECHNICAL FIELD

The present invention relates to a wire rope flaw detector for detecting a damage in a wire rope that suspends a passenger car, such as an elevator.

BACKGROUND ART

One means for detecting a damage in a wire rope or a break in an element wire is a wire rope flaw detector as described in PTL 1 which uses a permanent magnet or electromagnet to magnetize a predetermined axial section of a wire rope that runs at a constant speed and uses a magnetic sensor placed in the predetermined section to detect a leakage flux leaking from a damaged area of the wire rope.

In such a wire rope flaw detector, a coil is employed as a magnetic sensor for detecting a leakage flux, which is formed generally U-shaped so as to surround almost a half circumference of a wire rope.

Furthermore, a protection plate made of a non-magnetic material having a capability of protecting the coil from the sliding of the rope, and a pole piece of a ferromagnetic material that is positioned between the permanent magnet and the wire rope while supporting the protection plate and that reduces the magnetoresistance between the permanent magnet and the wire rope are also formed so as to have a generally U-shaped cross section, all of which are integrated to form a probe.

The PTL 1 also has suggested a structure in which a magnetizer composed of a permanent magnet (or electromagnet) and a back yoke can be separated from the probe.

This structure may be because, since the cross section of the probe is generally U-shaped with a particular radius, a probe having a generally U-shaped cross section with a different radius needs to be used as appropriate for a wire rope having a different diameter.

CITATION LIST

Patent Literature

PTL 1: JP-A-9-210968

SUMMARY OF INVENTION

Technical Problem

As described above, the wire rope flaw detector disclosed in the PTL 1 needs to use a generally U-shaped probe having a radius slightly larger than the diameter of a wire rope to be flaw-detected and close to the diameter of the wire rope.

Because, when the radius of the generally U-shape is excessively larger than the wire rope, the gap between the wire rope and the coil except a portion in which the wire rope is in contact with the protection plate becomes larger, then, if a damaged area of the wire rope is far away from the portion in contact with the protection plate in the circumferential direction of the wire rope, the leakage flux cannot sufficiently reach the coil, which reduces the voltage induced in the coil and decreases the S/N of the flaw detection.

Accordingly, when an operator visits a field in which a plurality of wire rope diameters exist, the operator needs to carry a plurality of probes, so the load on the operator due to increase in the weight and volume of the probes could be of concern.

Furthermore, for a probe composed of a plurality of parts each having a generally U-shaped cross section, the machining cost of the individual parts tends to be high.

Among others, the coil needs to have many turns in a limited area in order to increase the amount of interlinkage flux, so an extra-fine wire (with a wire diameter of 40 μm or so) is often used for the coil. Forming such a wire material into a U-shape without damaging the material requires a sophisticated technique, which significantly increases the machining cost with respect to that for a coil with no generally U-shape formed.

Furthermore, a guide plate for protecting the coil, a pole piece for supporting the guide plate and, possibly, an iron core fitted around the coil in order to increase the amount of interlinkage flux are all required to be generally U-shaped.

On the other hand, in order to achieve a certain level of detection accuracy, the machining tolerance of these parts are required to be more than a dozen micrometers to one-hundred micrometers, so these parts also contribute to increase in the machining cost.

Generally, the cost of the generally U-shaped parts accounts for a very large portion of the overall manufacturing cost of the wire rope flaw detector.

Hence, the need for possessing a plurality of probes composed of such expensive parts increases the amount of investment in an inspection equipment, which may press management of an inspection agency.

In order to solve the above problem, it is an object of the present invention to provide a wire rope flaw detector that is capable of accommodating a plurality of wire rope diameters and is inexpensive.

Solution to Problem

The invention provides a wire rope flaw detector that has a magnetizer placed therein for forming a magnetic circuit for magnetizing a predetermined longitudinal section of a wire rope and detects a leakage flux leaking from a damaged area of the wire rope in the predetermined section to detect a damage of the wire rope, the wire rope flaw detector including: at least two magnetic sensor units that are integrated with the magnetizer and include planer coils placed opposite to each other with the magnetic circuit in between, in the direction almost parallel to the magnetic circuit in the predetermined section; and an adjuster capable of changing the distance between the at least two magnetic sensor units depending on the diameter of the wire rope.

Advantageous Effects of Invention

According to the wire rope flaw detector of the invention, by combining a plurality of magnetic sensor units including planer coils, an area of a wire rope that is equal to or wider than the antecedent can be covered, and, by providing an adjuster capable of changing the distance between a plurality of magnetic sensor units placed opposite to each other, a wire rope flaw detector that is capable of accommodating a plurality of wire rope diameters and is inexpensive can be provided.

DESCRIPTION OF EMBODIMENTS

First Embodiment

Figure 1:
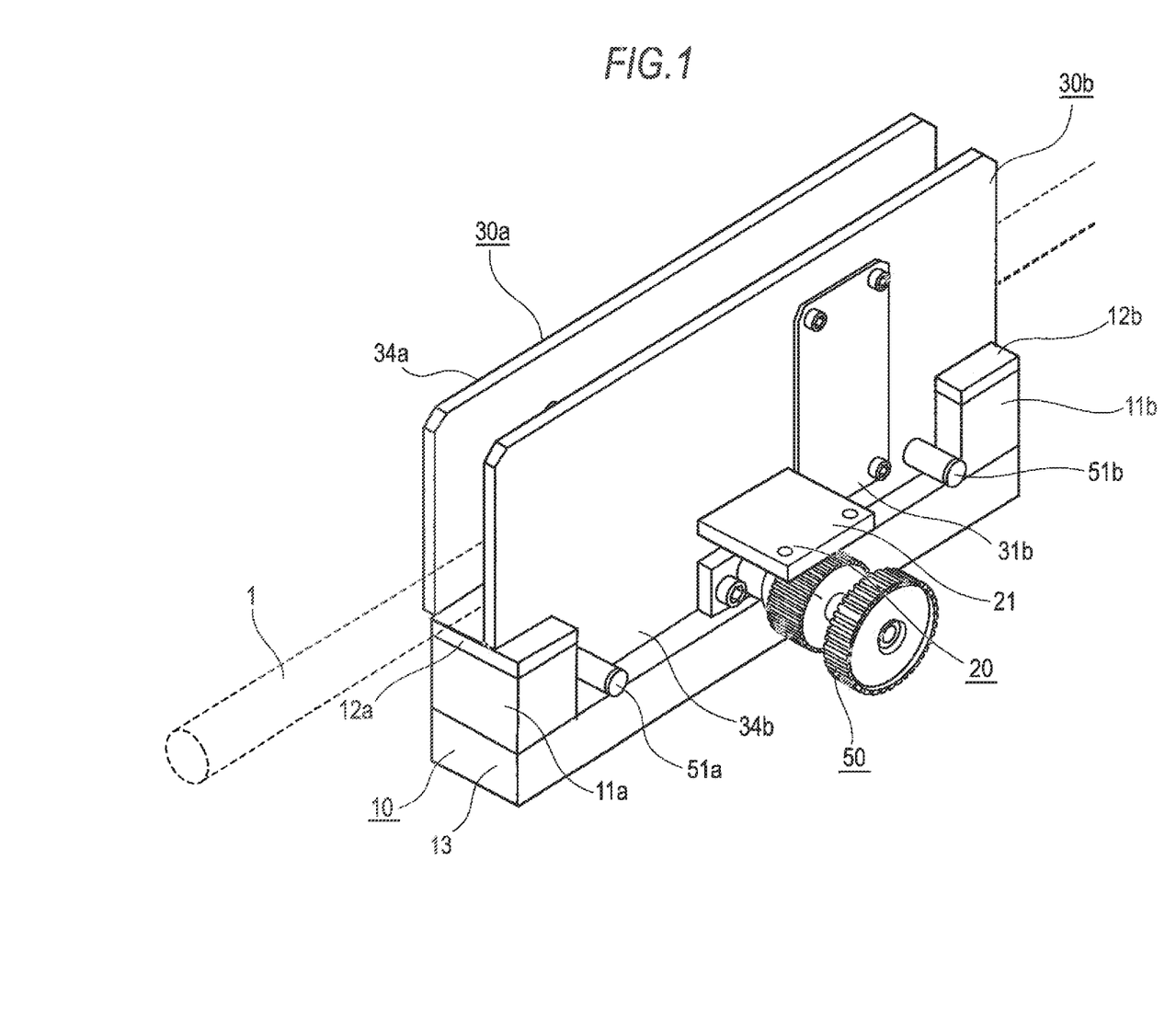
FIG. 1 A perspective view showing a wire rope flaw detector in accordance with a first embodiment of the invention.
Figure 2:
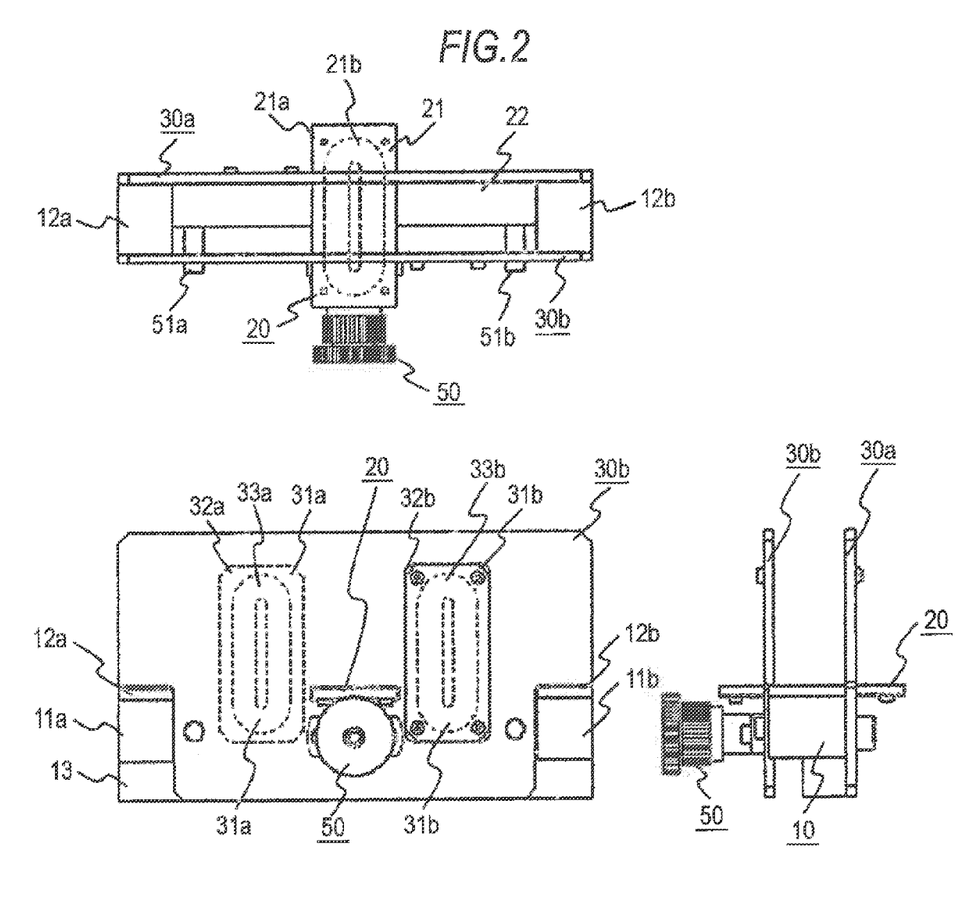
FIG. 2 A three-view drawing showing the wire rope flaw detector of FIG. 1.

FIG. 1 is a perspective view showing a wire rope flaw detector in accordance with a first embodiment of the invention. FIG. 2 is a three-view drawing showing the wire rope flaw detector of FIG. 1.

The wire rope flaw detector in accordance with the first embodiment includes: a magnetizer 10 for forming a magnetic circuit for magnetizing a predetermined longitudinal section of a wire rope; a plurality of magnetic sensor units 20 and 30 for detecting a leakage flux leaking from a damaged area of the wire rope in the predetermined section; and an adjuster 50 capable of changing the distance between the plurality of magnetic sensor units placed opposite to each other depending on the diameter of the wire rope.

The magnetizer 10 includes: two permanent magnets 11a and 11b that are placed at the positions corresponding to the both ends of the predetermined section and have pole pieces 12a and 12b on the side abutting against a wire rope 1; and a back yoke 13 that magnetically connects the opposite sides from the pole piece sides of the permanent magnets.

In the magnetizer 10, the pole pieces 12a and 12b, the permanent magnets 11a and 11b and the back yoke 13 are integrated to form a magnetic circuit 14 (see FIG. 6) for magnetizing a predetermined longitudinal section of the wire rope.

The permanent magnets 11a and 11b are selected to have a magnetomotive force sufficient for causing the flux density in the wire rope to reach the saturation region.

A magnetic sensor unit for detecting a leakage flux 1b leaking from a damaged area 1a of the wire rope 1 includes: a center sensor unit 20 that is placed at almost the center of the back yoke 13 of the magnetizer 10 in the direction almost perpendicular to the magnetic circuit 14; and furthermore, two side sensor units 30a and 30b that are placed with the magnetic circuit 14 in between, in the direction almost parallel to the magnetic circuit 14.

The center sensor unit 20 includes a sensor body 21 and a non-magnetic sliding member 22. The sensor body 21 includes a planar coil 21b buried in a non-magnetic plate 21a. In order to guide the wire rope 1 so that the wire rope 1 slides on the same plane as the pole pieces 12a and 12b, the sliding member 22 includes a non-magnetic sliding member 17 attached onto the back yoke 13 of the magnetizer 10 across the two permanent magnets 11a and 11b.

The two side sensor units 30a and 30b include sensor bodies 31a and 31b and non-magnetic guide plates 34a and 34b. The sensor bodies 31a and 31b include planer coils 33a and 33b buried in non-magnetic plates 32a and 32b, respectively.

The guide plates 32a and 32b are placed parallel to each other with the magnetic circuit 14 in between in the predetermined section, with the sensor bodies 31a and 31b fixed with screws at the positions of the guide plates 32a and 32b, respectively, opposite to each other to the left and right of the predetermined section.

The guide plates 32a and 32b have a notch 35 near their center to pass the center sensor unit 20 through.

One side sensor unit 30a of the two side sensor units 30a and 30b is fixed to the center sensor unit 20.

Figure 3:
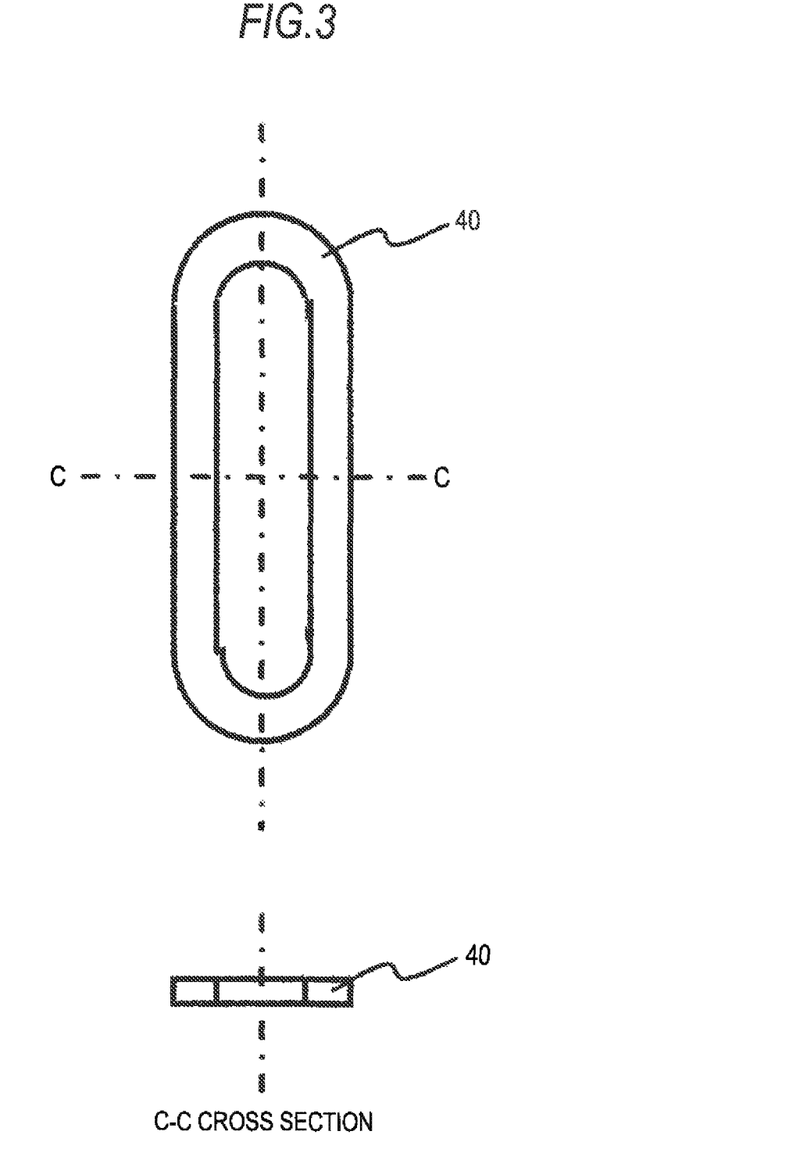
FIG. 3 A schematic view showing an example of a coil member used for a magnetic sensor unit.

FIG. 3 shows a coil member 40 used for the coils 21b, 33a and 33b of the center sensor unit 20 and the side sensor units 30a and 30b, respectively.

The coil member 40 is devised by winding several hundred to several thousand turns of a copper wire with a wire diameter of several tens of micrometers to increase a voltage induced across the coil when a break passes.

Unlike the case described in the PTL 1, since forming a generally U-shape is not performed, the fabrication steps only includes a step of winding a wire around a predetermined winding frame and then a step of fixing treatment (e.g., heating or alcohol dropping for self-welding wire).

Furthermore, the non-magnetic plates 21a, 32a and 32b of the center sensor unit 20 and the side sensor units 30a and 30b, respectively, in which the coil member 40 is buried can also be manufactured basically by machining (e.g., grooving) a flat plate-like non-magnetic material from one direction, which eliminates the need for changing the way of holding the material and bending, to allow the machining cost to be reduced.

Figure 4:
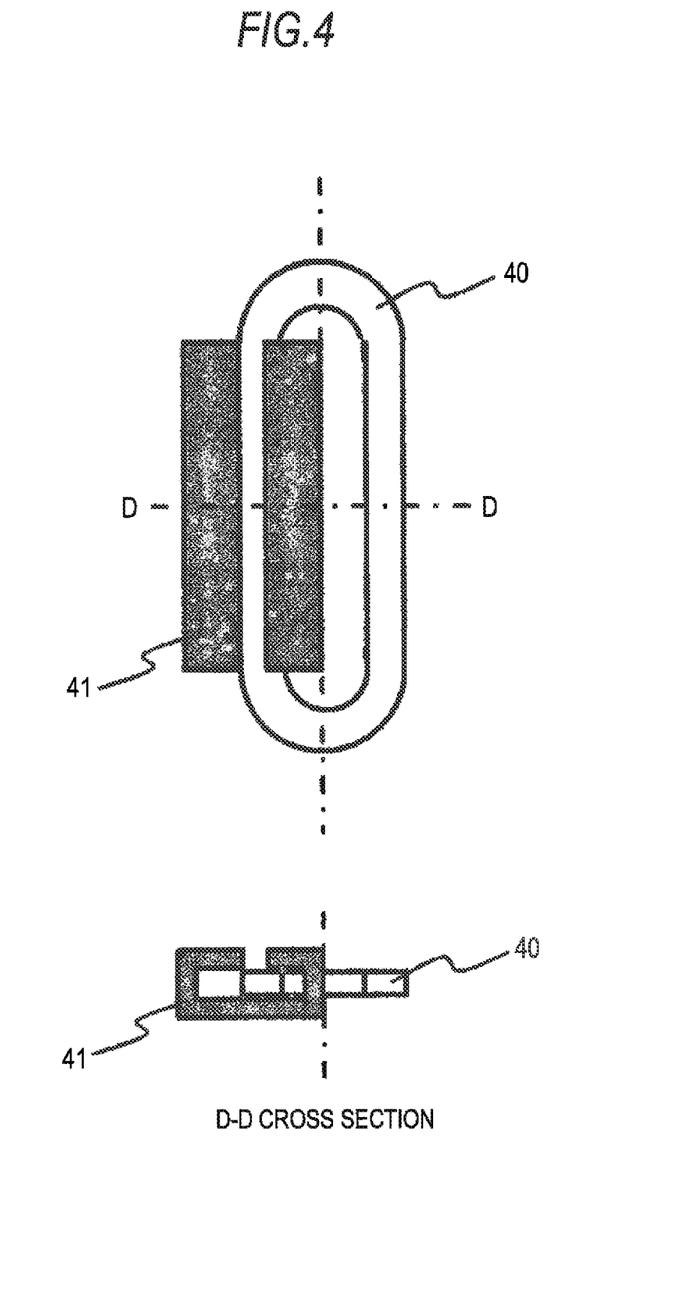
FIG. 4 A schematic view showing another example of the coil member used for the magnetic sensor unit.

Furthermore, an iron core 41 for increasing the amount of interlinkage flux may be fitted around the coil member 40 as shown in FIG. 4. In this case, the iron core is linearly machined, which is easier than machining the core into a generally U-shape, allowing the machining cost to be reduced.

Figure 5A:
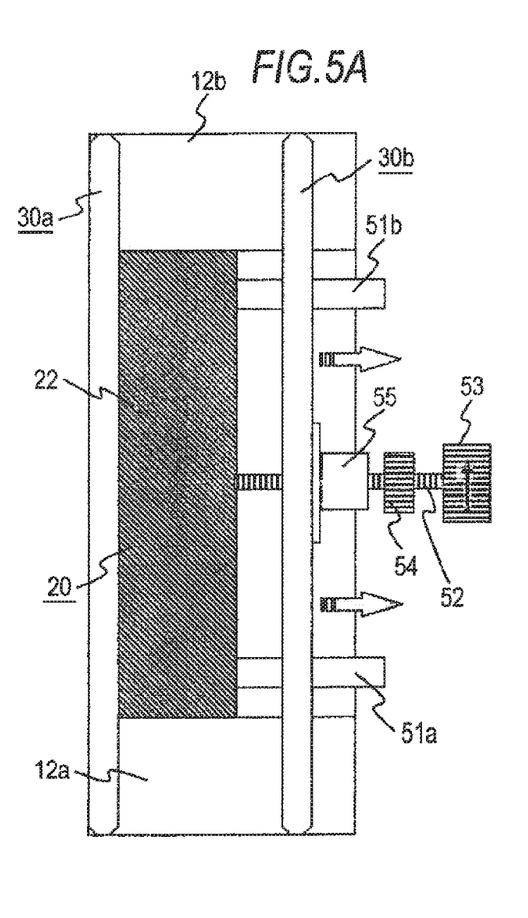
FIGS. 5A and 5B A schematic view showing a moving mechanism of the magnetic sensor unit of the wire rope flaw detector in accordance with the first embodiment.
Figure 5B:
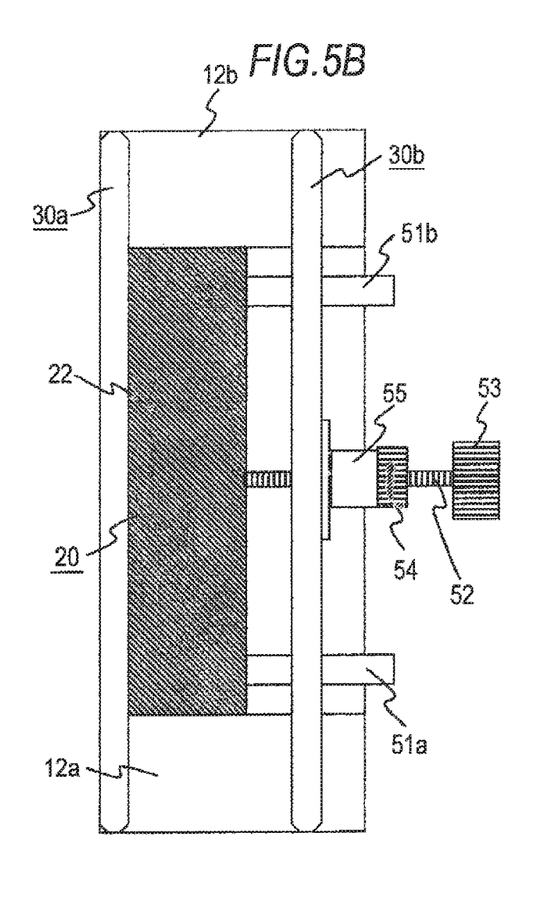

As shown in FIG. 5, the adjuster 50 can change the distance between the side sensor units 30a and 30b depending on the diameter of the wire rope 1 using a linear moving mechanism.

In FIG. 5, two guide shafts 51a and 51b are fixed to the center sensor unit 20, and a male screw 52 is attached to the center sensor unit 20 rotatably with its own center axis as a rotation axis.

The side sensor unit 30b has holes to pass the guide shafts 51a and 51b through, the diameter of which is set to have a fit tolerance that allows the guide shafts 51a and 51b to slide smoothly.

Furthermore, in order to stabilize the position of the movable side sensor unit 30b to be kept parallel to the stationary side sensor unit 30a, a screw holder 55 is employed as a female screw. An inspector turns a feed knob 53 of the screw end to cause the male screw 52 to rotate to move the side sensor unit 30b.

When the distance between the side sensor units 30a and 30b reaches a desired distance, a lock nut 54 is tightened into the screw holder 55 to lock the side sensor unit 30b.

Figure 6:
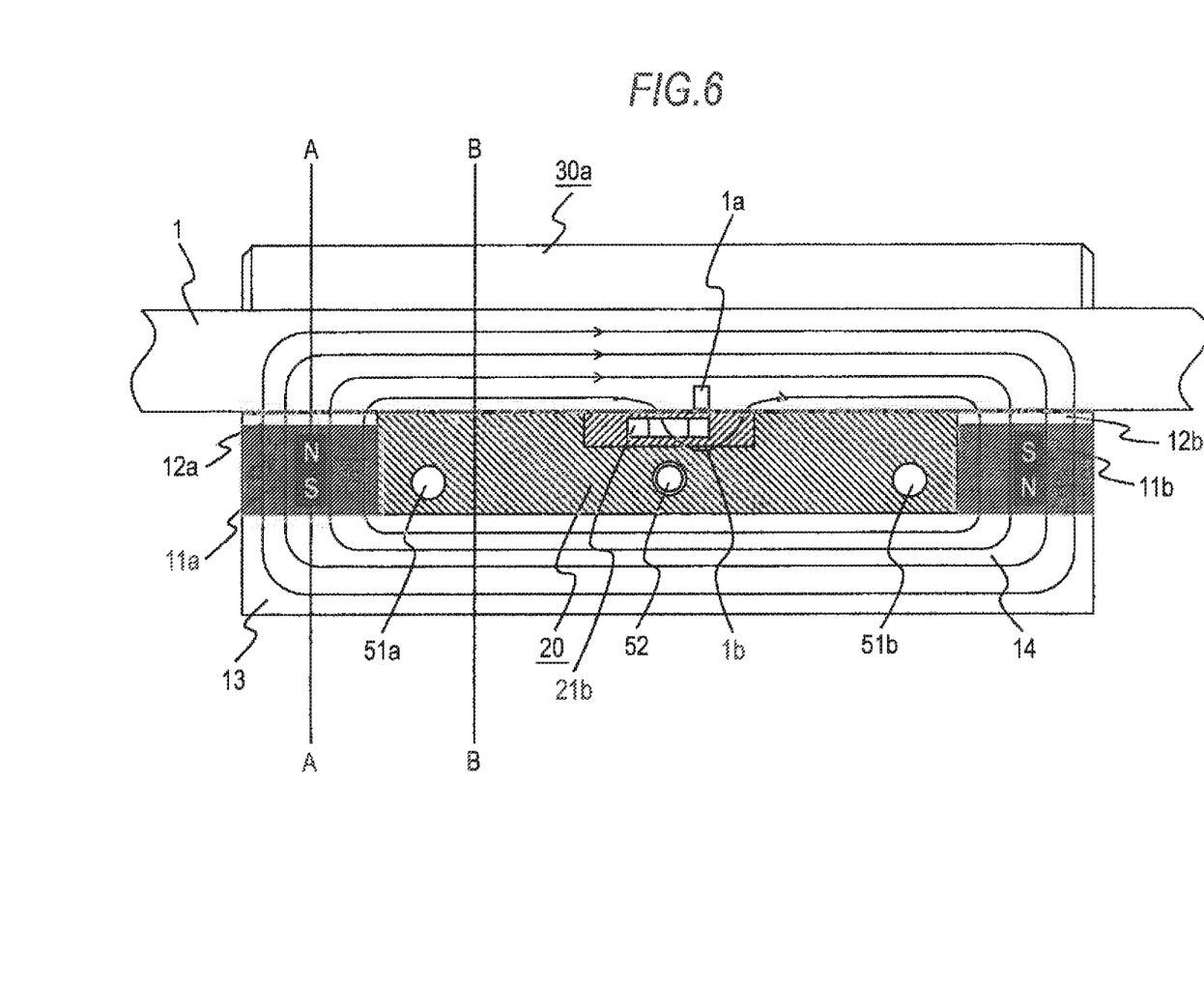
FIG. 6 A cross-sectional view of the wire rope flaw detector in accordance with the first embodiment taken along a plane passing the center axis of the wire rope.

As shown in FIG. 6, in the wire rope flaw detector in accordance with the first embodiment, since the wire rope 1 slides on the pole pieces 12a and 12b and the center sensor unit 20, the pole pieces 12a and 12b and the center sensor unit 20 are placed so as to have the slide planes having the same height.

Flux that has exited the permanent magnet 11a pass through the wire rope 1 via the pole piece 12a and enters the permanent magnet 11b via the pole piece 12b.

The wire ripe 1 is caused to relatively move with respect to the magnetizer 10. In this case, when the damaged area 1a of the wire rope enters a magnetized section between the pole pieces 12a and 12b, the leakage flux 1b leaks from the wire rope 1 around the damaged area 1a. When the leakage flux 1b is detected by any of the magnetic sensors surrounding the wire rope 1 on three sides, i.e., the center sensor unit 20 and the side sensor units 30a and 30b, the damage 1a on the wire rope 1 can be found.

Although a coil is employed as the magnetic sensor in the first embodiment, other detection methods may be used, such as one using a Hall element.

Figure 7A:
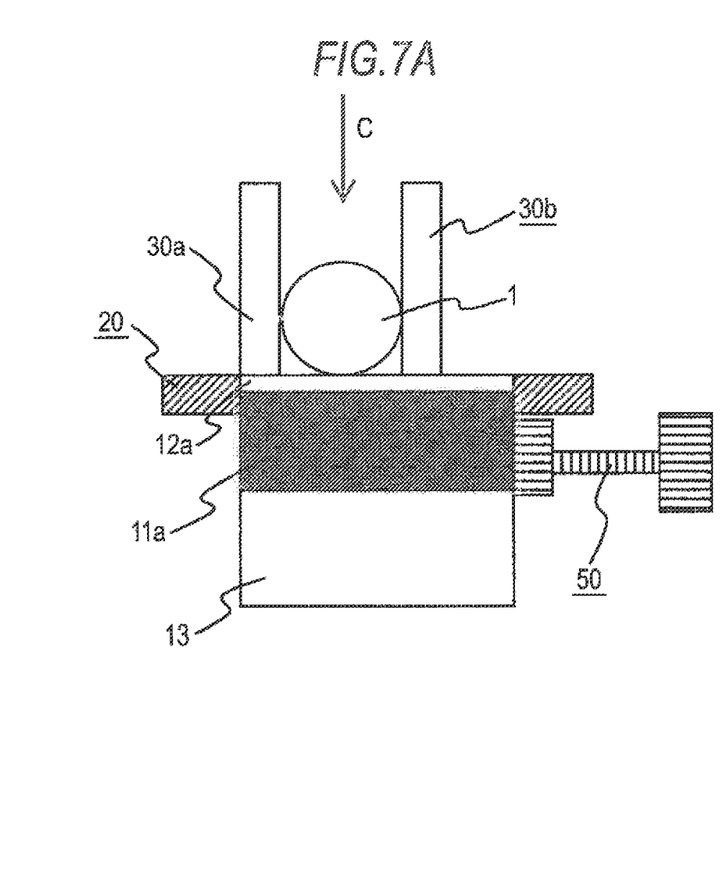
FIGS. 7A and 7B A cross-sectional view taken along the line A-A in FIG. 6.
Figure 7B:
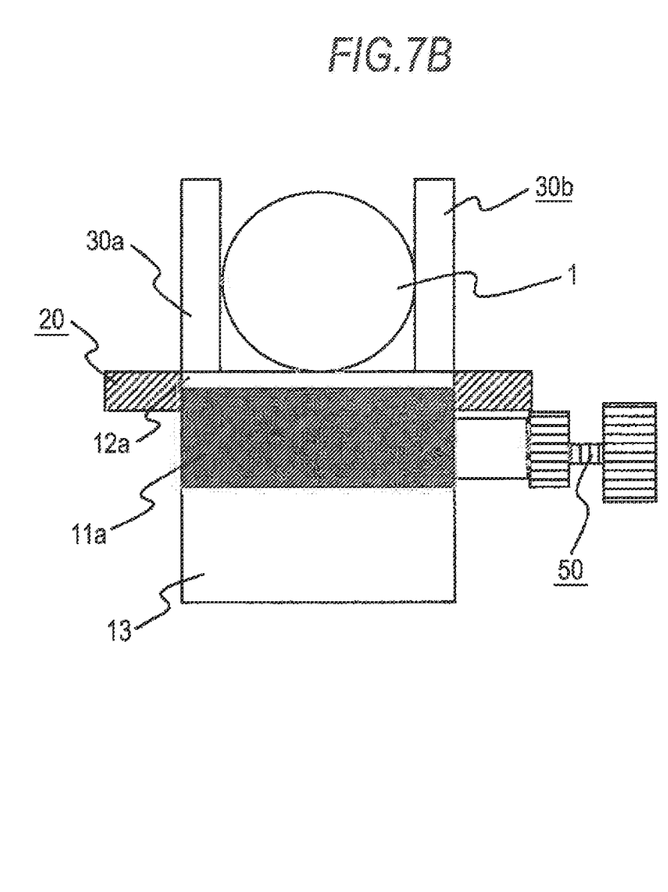

FIGS. 7A and 7B are cross-sectional views taken along the line A-A in FIG. 6 in inspecting a wire rope with the minimum and maximum diameter, respectively. The pole pieces 12a and 12b and the permanent magnets 11a and 11b have a width sufficient for the wire rope 1 with the maximum diameter to pass.

Figure 8A:
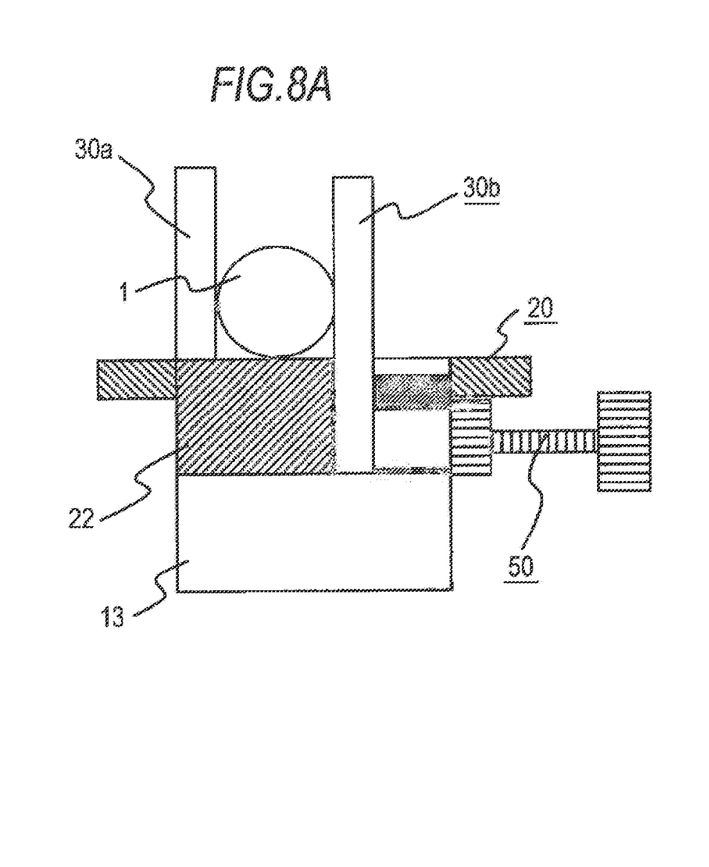
FIGS. 8A and 8B A cross-sectional view taken along the line B-B in FIG. 6.
Figure 8B:
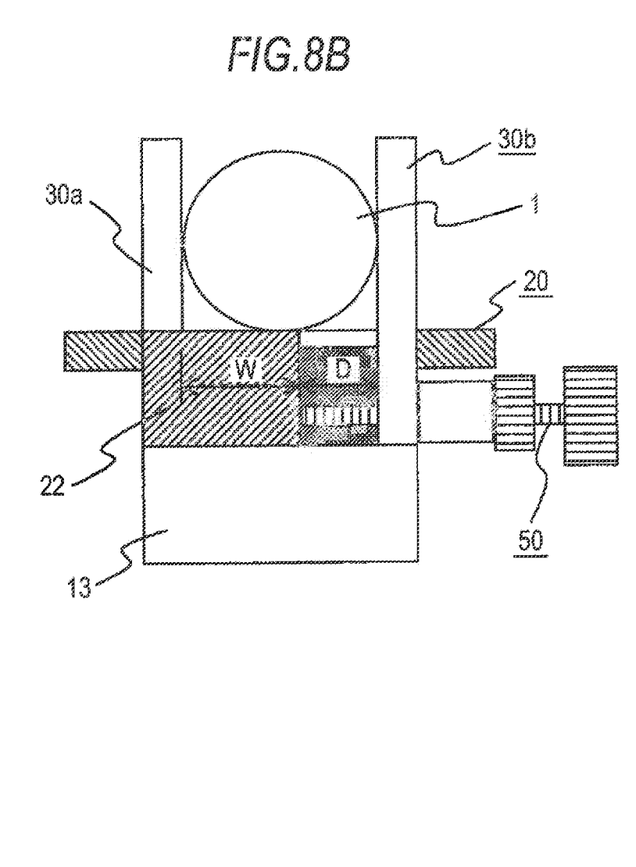

FIGS. 8A and 8B are cross-sectional views taken along the line B-B in FIG. 6. The position of the movable side sensor unit 30b when abutting against the center sensor unit 20 is a position for a wire rope with the minimum diameter.

On the other hand, the range of movement of the side sensor unit 30a is a range in which the gap D between the movable side sensor unit 30b and the center sensor unit 20 does not exceed the width W between the inner wall of the stationary side sensor unit 30a and the side of the movable side sensor unit 30b.

Because, when the gap D exceeds the width W, part of the wire rope 1 leaves the contact surface between the wire rope 1 and the center sensor unit 20, then an excessive load is put on the pole pieces 12a and 12b and the coil 21b of the center sensor unit 20, which may damage the wire rope or the wire rope flaw detector.

As described above, in the wire rope flaw detector in accordance with the first embodiment, the non-magnetic sliding member 22 is provided in the center sensor unit 20 between the two pole pieces 12a and 12b, then the contact surfaces between the wire rope 1 and the pole pieces and the sliding member are placed so as to be almost continuous between the contact surfaces, and then, when the distance between the side sensor units 30a and 30b that are generally parallel to each other is the maximum, the sliding member 22 exists at the position at which a virtual plane at the same distance from the both sensor and the sliding member 22 cross, which allows any wire rope 1 to be inspected to always slide smoothly on the pole pieces 12a and 12b and the sliding member 22.

Figure 9A:
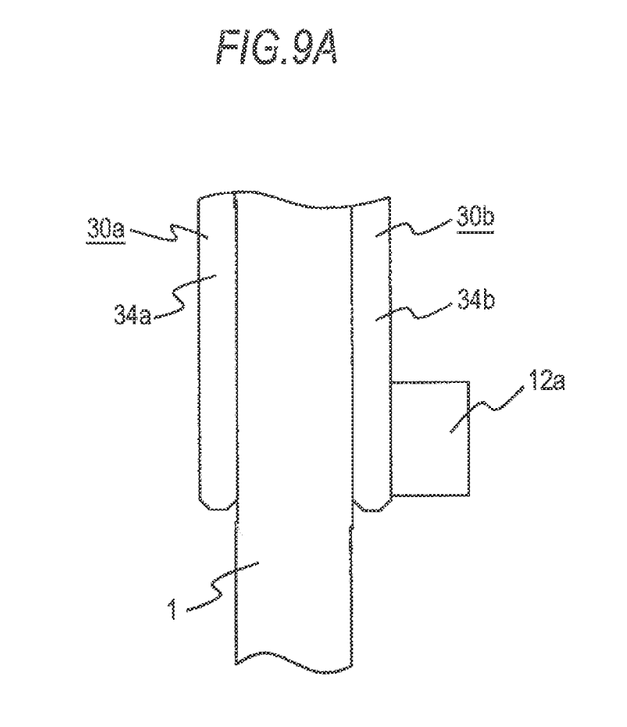
FIGS. 9A and 9B A schematic view seen from the direction indicated by the arrow C in FIG. 7.
Figure 9B:
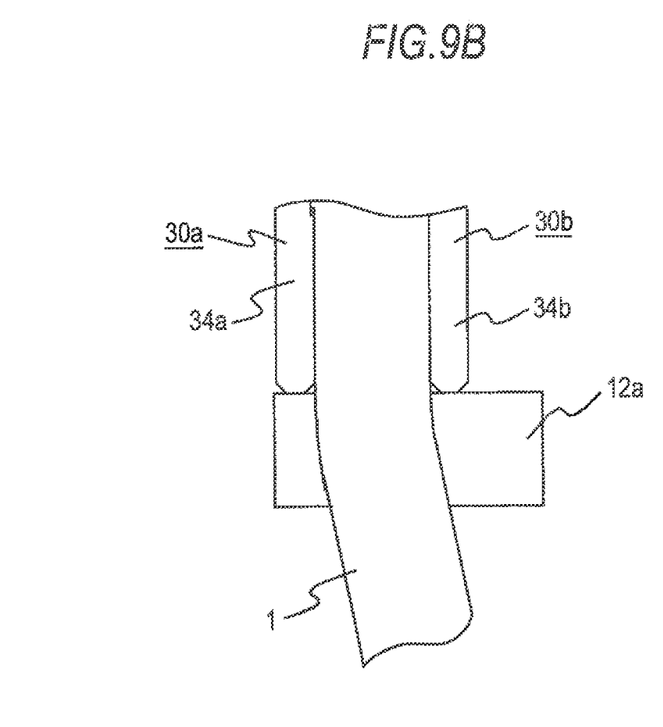

FIGS. 9A and 9B are schematic views of the wire rope flaw detector in accordance with the first embodiment seen from the direction indicated by the arrow C in FIG. 7, illustrating the vibration of the wire rope 1 at the ends of the side sensor units 30a and 30b.

As shown in FIG. 9A, the side sensor units 30a and 30b are placed such that the ends of the side sensor units 30a and 30b along the longitudinal direction of the rope fully overlap with the pole pieces 12a and 12b.

The reason for this is as follows.

The wire rope 1 that is moving is normally vibrating, the source of which are the contact between the twisting of the wire rope 1 and a sheave, the vibration of the car and the like.

Figure 10A:
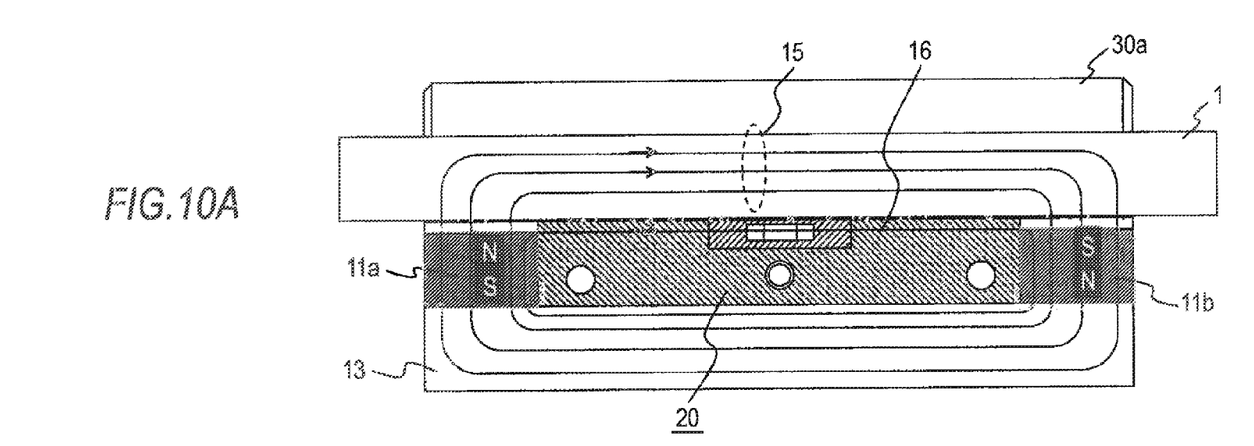
FIGS. 10A and 10B A cross-sectional view illustrating change in the flow of flux due to vibration of the wire rope.

Note that, if the side sensor units 30a and 30b do not overlap with the pole pieces 12a and 12b as shown in FIG. 9B, the wire rope 1 can move on the contact surfaces between the pole pieces 12a and 12b and the wire rope 1 immediately before and after entering or exiting the square U-shaped passage formed by the center sensor unit 20 and the side sensor units 30a and 30b. At these points, as shown in FIG. 10A, the amount of flux 15 entering the wire rope 1 changes and the amount of flux 16 not entering the wire rope but leaking out also changes.

Figure 10B:
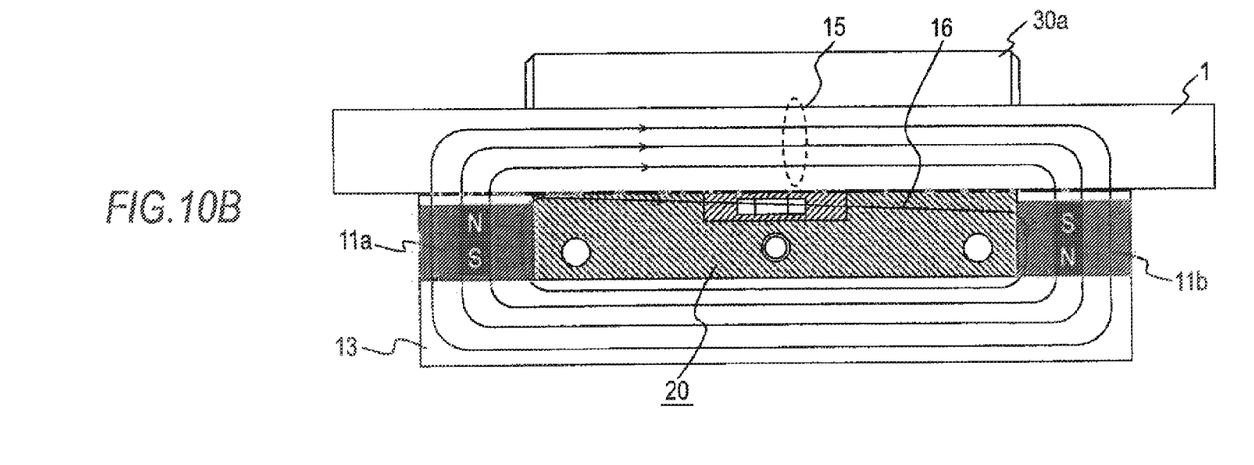

Since part of the flux 16 passes near the coil 22, the contact state between the wire rope 1 and the pole pieces 12a and 12b changes. Then, the change in these amount of flux causes the flow path of the flux 16 to change as shown in FIG. 10B, causing the amount of interlinkage flux of the coil 21b of the center sensor unit 20 to change, which induces a voltage in the coil 21b to generate a noise signal.

Thus, the guide plates 34a and 34b of the side sensor units 30a and 30b overlap with the pole pieces 12a and 12b as shown in FIG. 9A, which can suppress undesired movement of the wire rope 1 on the pole pieces 12a and 12b and reduce noise.

Second Embodiment

Figure 11:
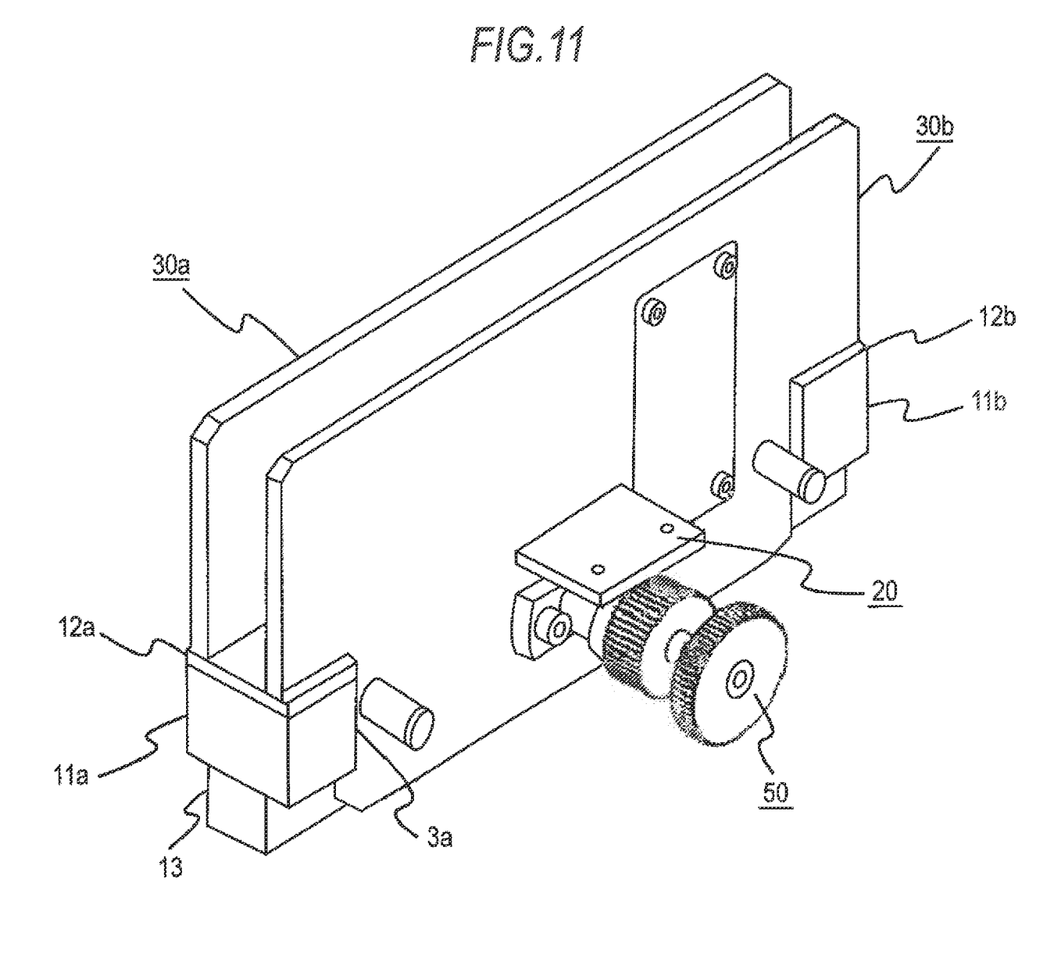
FIG. 11 A perspective view showing a wire rope flaw detector in accordance with a second embodiment.
Figure 12:
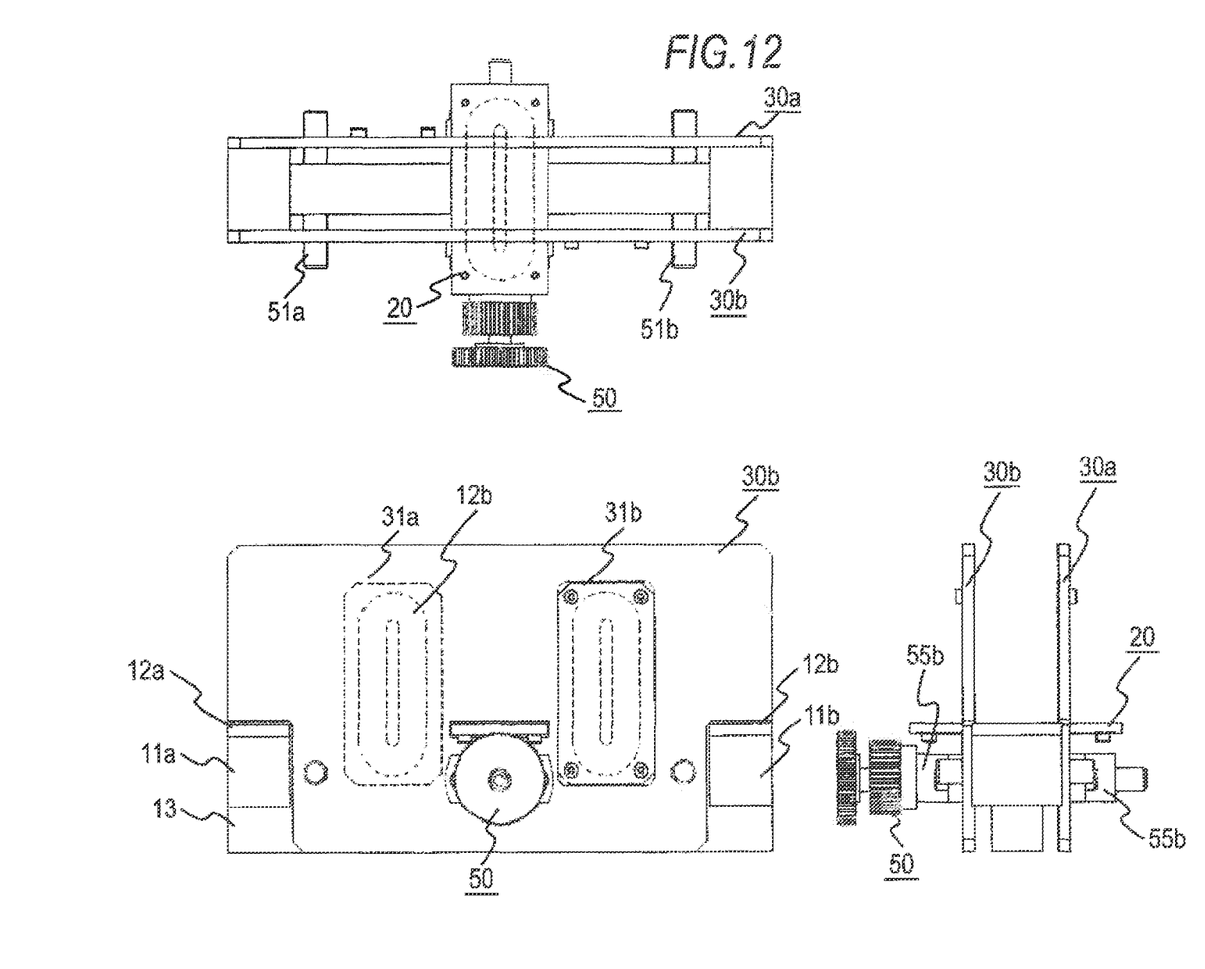
FIG. 12 A three-view drawing showing the wire rope flaw detector of FIG. 12.

FIG. 11 is a perspective view showing a wire rope flaw detector in accordance with a second embodiment. FIG. 12 is a three-view drawing showing the wire rope flaw detector of FIG. 11.

An adjuster 50 enables both of two side sensor units 30a and 30b to move using a linear moving mechanism having screw holders 55a and 55b. Such a function can be provided by using a reverse screw for the screw holder of one of the two side sensor units 30a and 30b, e.g., the screw holder 55b of the side sensor unit 30b.

This allows the wire rope 1 to be positioned at the center of the center sensor unit 20 irrespective of the diameter of the wire rope, which can expand the applicable range of the wire rope diameter.

Third Embodiment

Figure 13:
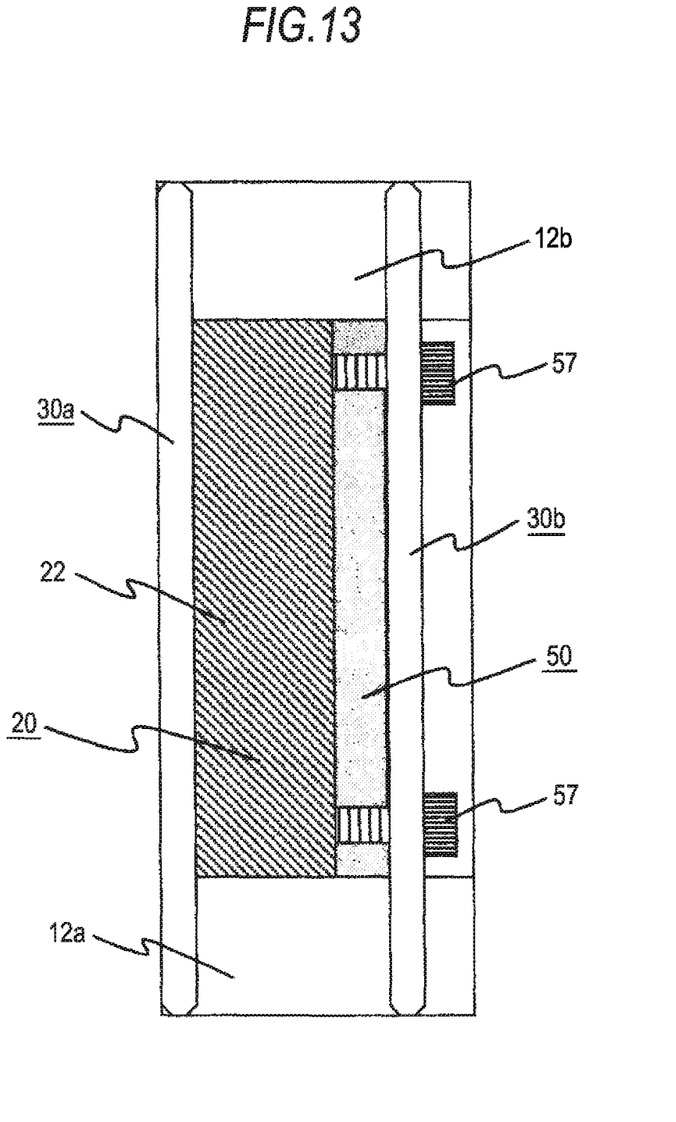
FIG. 13 A main part schematic view illustrating an adjuster of a wire rope flaw detector in accordance with a third embodiment.

FIG. 13 is a main part schematic view showing an adjuster of a wire rope flaw detector in accordance with a third embodiment.

A spacer 56 is inserted between two side sensor units 30a and 30b and fixed with screws 57, the spacer 56 having a width capable of setting the distance between the side sensor units 30a and 30b depending on the diameter of the wire rope 1. In this embodiment, unlike the first and second embodiments, the distance between the side sensor units 30a and 30b cannot be adjusted in a non-stage manner, but, if the number of applicable diameters of the wire rope 1 is small, this embodiment is more suitable due to lower manufacturing cost.

REFERENCE SIGNS LIST

1: wire rope, 1a: damaged area, 1b: leakage flux,
10: magnetizer, 11a, 11b: permanent magnet, 12a, 12b: pole piece,
13: back yoke, 14: magnetic circuit, 15, 16: flux,
20: center sensor unit, 21: sensor body,
21a: non-magnetic plate, 21b: coil, 22: sliding member,
30a, 30b: side sensor units, 31a, 31b: sensor body,
32a, 32b: non-magnetic plate, 33a, 33b: coil,
34a, 34b: guide plate, 35: notch, 40: coil member, 41: iron core,
50: adjuster, 51a, 51b: guide shaft,
52: male screw, 53: feed knob, 54: lock nut,
55a, 55b: screw holder, 56: spacer,
57: screw

The invention claimed is:

1. A wire rope flaw detector that has a magnetizer placed therein for forming a magnetic circuit for magnetizing a predetermined longitudinal section of a wire rope and detects a leakage flux leaking from a damaged area of the wire rope in the predetermined section to detect a damage of the wire rope, the wire rope flaw detector comprising:
   at least two magnetic sensor units that are integrated with the magnetizer and include planer coils placed opposite to each other with the magnetic circuit in between, in the direction almost parallel to the magnetic circuit in the predetermined section; and
   an adjuster capable of changing the distance between the at least two magnetic sensor units depending on the diameter of the wire rope.

2. The wire rope flaw detector according to claim 1, wherein the plurality of magnetic sensor units are two magnetic sensor units each having a planer coil embedded in a non-magnetic plate, the non-magnetic plates being placed in parallel to each other in the predetermined section, the distance between the two magnetic sensor units being adjusted by the adjuster.

3. The wire rope flaw detector according to claim 1, wherein the adjuster includes a linear moving mechanism for linearly moving at least one of the two magnetic sensor units with respect to the other.

4. The wire rope flaw detector according to claim 3, wherein the adjuster includes a linear moving mechanism for linearly moving both of the two magnetic sensor units with respect to the other.

5. The wire rope flaw detector according to claim 1, wherein the adjuster has a width capable of setting the distance between the two magnetic sensor units depending on the diameter of the wire rope and includes a spacer placed between the two magnetic sensor units.

6. The wire rope flaw detector according to claim 1, wherein the magnetizer includes: two permanent magnets that are placed at the positions corresponding to the both ends of the predetermined section and have pole pieces on the side abutting against the wire rope; and a back yoke that magnetically connects the opposite sides from the pole piece sides of the permanent magnets.

7. The wire rope flaw detector according to claim 1, further comprising a second magnetic sensor unit that is placed at the center of the predetermined section in the direction almost perpendicular to the magnetic circuit and detects the leakage flux.

8. The wire rope flaw detector according to claim 7, wherein the second magnetic sensor unit comprises a non-magnetic sliding member so that a contact surface with the wire rope is continuously formed between the pole pieces of the two permanent magnets.

9. The wire rope flaw detector according to claim 8, wherein the sliding member exists at the position at which a virtual plane at the same distance from the two magnetic sensor units and the sliding member cross when the distance between the two magnetic sensor units is the maximum.

* * * * *